(12) United States Patent
Kim et al.

(10) Patent No.: US 12,237,467 B2
(45) Date of Patent: Feb. 25, 2025

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Energy Solution, Ltd., Seoul (KR)

(72) Inventors: Hyun Seung Kim, Daejeon (KR); Yu Ha An, Daejeon (KR); Chul Haeng Lee, Daejeon (KR); Jeong Woo Oh, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 602 days.

(21) Appl. No.: 17/607,566

(22) PCT Filed: Aug. 21, 2020

(86) PCT No.: PCT/KR2020/011162
§ 371 (c)(1),
(2) Date: Oct. 29, 2021

(87) PCT Pub. No.: WO2021/034141
PCT Pub. Date: Feb. 25, 2021

(65) Prior Publication Data
US 2022/0223911 A1 Jul. 14, 2022

(30) Foreign Application Priority Data
Aug. 21, 2019 (KR) .................. 10-2019-0102521

(51) Int. Cl.
*H01M 10/0567* (2010.01)
*C07D 233/60* (2006.01)
*H01M 10/0525* (2010.01)

(52) U.S. Cl.
CPC ...... *H01M 10/0567* (2013.01); *C07D 233/60* (2013.01); *H01M 10/0525* (2013.01); *H01M 2300/0025* (2013.01)

(58) Field of Classification Search
CPC .......... H01M 10/0525; H01M 10/0567; C07D 233/60
See application file for complete search history.

(56) References Cited

U.S. PATENT DOCUMENTS

2014/0272604 A1 9/2014 Lim et al.
2015/0140445 A1 5/2015 Aoki et al.
(Continued)

FOREIGN PATENT DOCUMENTS

CN 104781976 A 7/2015
CN 113678298 A 11/2021
(Continued)

OTHER PUBLICATIONS

Extended European Search Report for Application No. 20855458.4 dated Jun. 15, 2022. 7 pgs.
(Continued)

*Primary Examiner* — Karie O'Neill Apicella
(74) *Attorney, Agent, or Firm* — Lerner David LLP

(57) ABSTRACT

A non-aqueous electrolyte solution and a lithium secondary battery including the same are disclosed herein. In some embodiments, a non-aqueous electrolyte solution for a lithium secondary battery includes a lithium salt, an organic solvent, a compound represented by Formula 1 as a first additive, and lithium difluorophosphate as a second additive, wherein a weight ratio of the first additive to the second additive is in a range of 1:2 to 1:10.

7 Claims, 1 Drawing Sheet

(56) References Cited

U.S. PATENT DOCUMENTS

| | | | |
|---|---|---|---|
| 2018/0358655 A1 | 12/2018 | Kono et al. | |
| 2020/0044287 A1* | 2/2020 | Kim | H01M 10/052 |
| 2020/0052322 A1* | 2/2020 | Yu | H01M 10/0525 |
| 2020/0251777 A1 | 8/2020 | Lim et al. | |
| 2022/0140391 A1 | 5/2022 | Kim et al. | |

FOREIGN PATENT DOCUMENTS

| | | | | |
|---|---|---|---|---|
| EP | 3913719 A1 | | 11/2021 | |
| JP | 2011049153 A | | 3/2011 | |
| JP | 2012-204100 A | | 10/2012 | |
| KR | 20140104383 A | | 8/2014 | |
| KR | 20190008100 A | | 1/2019 | |
| KR | 20190033448 A | * | 3/2019 | H01M 10/052 |
| KR | 20190059256 A | | 5/2019 | |
| KR | 20190092880 A | | 8/2019 | |
| WO | 2013187073 A1 | | 12/2013 | |
| WO | 2019013501 A1 | | 1/2019 | |

OTHER PUBLICATIONS

International Search Report for PCT/KR2020/011162 dated Nov. 30, 2020. 2 pgs.
Steven E. Sloop et al., "The role of Li-ion battery electrolyte reactivity in performance decline and self-discharge", Journal of Power Sources, 2003, 119-121. (2003). pp. 330-337.
H. H. Lee et al., "Thermal Stability of theSolid Electrolyte Interface on Carbon Electrodes of Lithium Batteries", Journal of The Electrochemical Society, 2004, 151 (4). (2004) pp. A542-A547.

* cited by examiner

[FIG. 1]
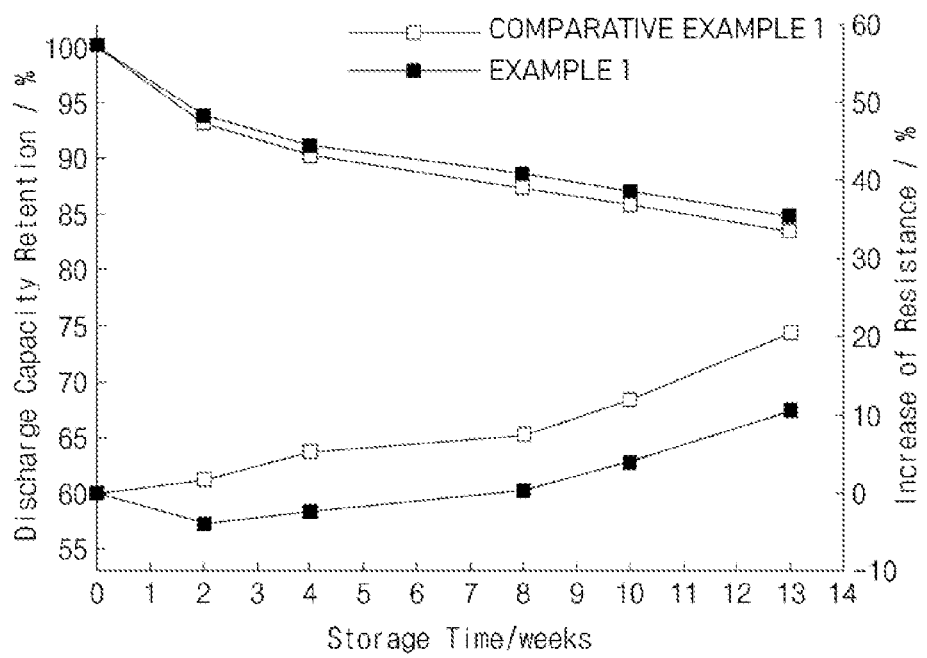
[FIG. 2]
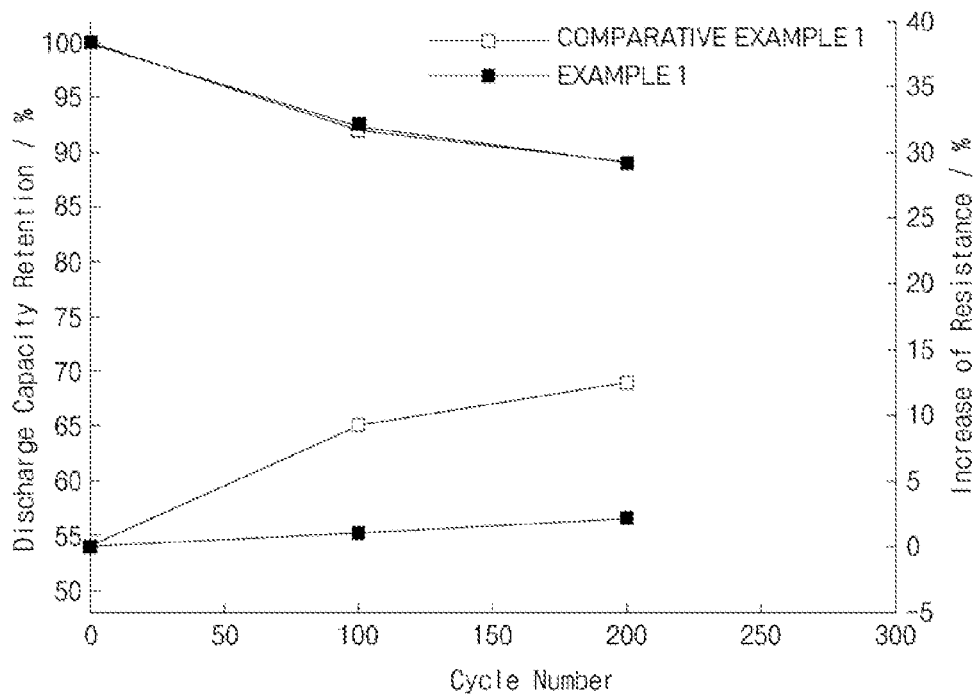

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2020/011162, filed on Aug. 21, 2020, which claims priority from Korean Patent Application No. 10-2019-0102521, filed on Aug. 21, 2019, the disclosures of which are incorporated by reference herein.

TECHNICAL FIELD

The present invention relates to a non-aqueous electrolyte solution for a lithium secondary battery, which includes a non-aqueous electrolyte solution additive having an excellent effect of scavenging a decomposition product generated from a lithium salt, and a lithium secondary battery in which high-temperature storage characteristics and high-temperature life characteristics are improved by including the same.

BACKGROUND ART

There is a need to develop technology for efficiently storing and utilizing electrical energy as personal IT devices and computer networks are developed with the development of information society and the accompanying dependency of society as a whole on the electrical energy is increased.

Among the technologies developed for this purpose, a technology based on secondary batteries is the most suitable technology for various applications. Since a secondary battery may be miniaturized to be applicable to a personal IT device and may be applied to an electric vehicle and a power storage device, there emerges an interest in the secondary battery. Lithium ion batteries are in the spotlight as battery systems having the theoretically highest energy density among these secondary battery technologies, and are currently being used in various devices.

The lithium ion battery is composed of a positive electrode formed of a transition metal oxide containing lithium, a negative electrode formed of a carbon-based material, such as graphite, capable of storing lithium, an electrolyte solution that becomes a medium for transferring lithium ions, and a separator, and it is important to properly select these components in order to improve electrochemical properties of the battery.

The lithium ion battery has a disadvantage in that an increase in resistance and a decrease in capacity occur during charge and discharge or storage at high temperatures to degrade performance. One of causes of such a problem, which has been suggested, is a side reaction caused by deterioration of the electrolyte solution at high temperatures, particularly deterioration due to decomposition of a lithium salt.

$LiPF_6$ has been mainly been used as the lithium salt to obtain suitable characteristics of the secondary battery, wherein, since a $PF_6^-$ anion of the lithium salt is very vulnerable to heat, it is known that a Lewis acid, such as $PF_5$, is generated due to pyrolysis when the battery is exposed to high temperatures.

The $PF_5$ thus formed not only causes a decomposition reaction of an organic solvent such as ethylene carbonate, but also destructs a solid electrolyte interphase (SEI) formed on a surface of an active material, such as graphite, having an operating voltage outside an electrochemical stabilization window of the electrolyte solution to cause additional decomposition of the electrolyte solution and the resulting increase in resistance and degradation of lifetime of the battery.

Thus, various methods have been proposed for maintaining passivation ability of the SEI when exposed to heat and suppressing degradation behavior of the battery by scavenging $PF_5$ which is formed by the pyrolysis of the $LiPF_6$-based salt.

DISCLOSURE OF THE INVENTION

Technical Problem

An aspect of the present invention provides a non-aqueous electrolyte solution for a lithium secondary battery which includes a non-aqueous electrolyte solution additive having an excellent effect of strengthening a solid electrolyte interphase (SEI) and an excellent effect of scavenging a decomposition product generated from a lithium salt in the electrolyte solution.

Another aspect of the present invention provides a lithium secondary battery in which an effect of improving high-temperature durability is excellent by including the non-aqueous electrolyte solution for a lithium secondary battery.

Technical Solution

According to an aspect of the present invention, there is provided a non-aqueous electrolyte solution for a lithium secondary battery which includes:
  a lithium salt;
  an organic solvent;
  a compound represented by Formula 1 as a first additive; and
  lithium difluorophosphate ($LiPO_2F_2$, hereinafter, referred to as "LiDFP") as a second additive,
  wherein a weight ratio of the first additive to the second additive is in a range of 1:2 to 1:10.

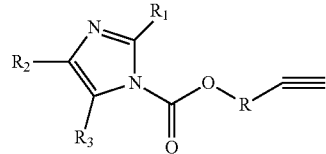

[Formula 1]

In Formula 1,
  R is a substituted or unsubstituted alkylene group having 1 to 3 carbon atoms, and
  $R_1$ to $R_3$ are each independently hydrogen, an alkyl group having 1 to 3 carbon atoms, or a nitrile group.

According to another aspect of the present invention, there is provided a lithium secondary battery including a positive electrode, a negative electrode, a separator, and the non-aqueous electrolyte solution for a lithium secondary battery of the present invention.

Advantageous Effects

A non-aqueous electrolyte solution for a lithium secondary battery of the present invention may form a robust film on surfaces of a positive electrode and a negative electrode by including a first additive, as a Lewis base material, and a second additive having an excellent film-forming effect in a specific ratio.

Also, a lithium secondary battery having improved high-temperature durability may be prepared by using the non-aqueous electrolyte solution of the present invention.

BRIEF DESCRIPTION OF THE DRAWINGS

FIG. 1 is a graph illustrating discharge capacity retentions and resistance increase rates after high-temperature (60° C.) storage of a secondary battery of Example 1 and a secondary battery of Comparative Example 1; and FIG. 2 is a graph illustrating discharge capacity retentions and resistance increase rates during 200 cycles at a high temperature (45° C.) of the secondary battery of Example 1 and the secondary battery of Comparative Example 1.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

In the present specification, the expression "substituted or unsubstituted" means that a compound is substituted with at least one substituent selected from deuterium, a halogen group, a hydroxy group, an amino group, a thiol group, a nitro group, a nitrile group, a silyl group, and a linear or branched $C_1$-$C_6$ alkoxy group, or does not have any substituent.

In the present specification, an alkylene group means one with two bonding sites in an alkane, that is, a divalent group. A description of an alkyl group may be applied except that it is a divalent group.

With respect to a lithium secondary battery, high-temperature storage characteristics are improved by forming a film having passivation ability on surfaces of a positive electrode and a negative electrode while a non-aqueous electrolyte solution is decomposed during initial charge and discharge. However, the film may be degraded by an acid, such as HF and $PF_5$, formed by pyrolysis of a lithium salt ($LiPF_6$, etc.) widely used in a lithium ion battery. Since surface resistance of the electrode is increased due to a change in structure of the surface while dissolution of transition metal elements occurs in the positive electrode by attack of the acid and theoretical capacity is reduced as the metallic elements, as redox centers, are lost, capacity may be reduced. Also, since transition metal ions thus dissolved are electrodeposited on the negative electrode reacting in a strong reduction potential range to not only consume electrons, but also destruct the film when electrodeposited to expose the surface of the negative electrode, an additional electrolyte decomposition reaction is caused. As a result, resistance of the negative electrode is increased, and capacity of a cell may be continuously reduced while irreversible capacity is increased.

Thus, the present invention attempts to provide a non-aqueous electrolyte solution, which may strengthen a solid electrolyte interphase (SEI) on the negative electrode while being able to prevent transition metal dissolution from the positive electrode or degradation of the SEI during high-temperature storage by scavenging the acid caused by the decomposition of the lithium salt by including a Lewis base-based additive as a non-aqueous electrolyte solution additive in the battery, and a lithium secondary battery including the same.

Non-aqueous Electrolyte Solution for Lithium Secondary Battery

First, a non-aqueous electrolyte solution for a lithium secondary battery according to the present invention will be described.

The non-aqueous electrolyte solution for a lithium secondary battery of the present invention includes (1) a lithium salt, (2) an organic solvent, (3) a compound represented by the following Formula 1 as a first additive, and (4) lithium difluorophosphate (LiDFP) as a second additive, wherein the first additive and the second additive are included in a weight ratio of 1:2 to 1:10.

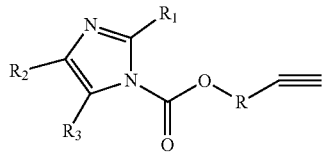

[Formula 1]

In Formula 1,

R is a substituted or unsubstituted alkylene group having 1 to 3 carbon atoms, and $R_1$ to $R_3$ are each independently hydrogen, an alkyl group having 1 to 3 carbon atoms, or a nitrile group.

(1) Lithium Salt

First, in a non-aqueous electrolyte solution for a lithium secondary battery according to an embodiment of the present invention, any lithium salt typically used in an electrolyte solution for a lithium secondary battery may be used as the lithium salt without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $B_{10}Cl_{10}^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CH_3SO_3^-$, $CF_3(CF_2)_7SO_3^-$, $CF_3CO_2^-$, $CH_3CO_2^-$, $SCN^-$, and $(CF_3CF_2SO_2)_2N^-$ as an anion. Specifically, the lithium salt may include at least one selected from the group consisting of LiCl, LiBr, LiI, $LiBF_4$, $LiClO_4$, $LiAlO_4$, $LiAlCl_4$, $LiPF_6$, $LiSbF_6$, $LiAsF_6$, $LiB_{10}Cl_{10}$, LiBOB(LiB($C_2O_4$)$_2$), $LiCF_3SO_3$, LiTFSI (LiN($SO_2CF_3$)$_2$), LiFSI(LiN($SO_2F$)$_2$), $LiCH_3SO_3$, $LiCF_3CO_2$, $LiCH_3CO_2$, and LiBETI (LiN($SO_2CF_2CF_3$)$_2$). More specifically, the lithium salt may include a single material selected from the group consisting of $LiBF_4$, $LiClO_4$, $LiPF_6$, LiBOB(LiB($C_2O_4$)$_2$), $LiCF_3SO_3$, LiTFSI(LiN($SO_2CF_3$)$_2$), LiFSI(LiN($SO_2F$)$_2$), and LiBETI (LiN($SO_2CF_2CF_3$)$_2$), or a mixture of two or more thereof.

The lithium salt may be appropriately changed in a normally usable range, but may be included in a concentration of 0.8 M to 3.0 M, for example, 1.0 M to 3.0 M in the electrolyte solution to obtain an optimum effect of forming a film for preventing corrosion of a surface of an electrode.

If the concentration of the lithium salt is less than 0.8 M, since mobility of lithium ions is reduced, capacity characteristics may be degraded, and, if the concentration of the lithium salt is greater than 3.0 M, since viscosity of the non-aqueous electrolyte solution is excessively increased, electrolyte wetting may be reduced and a film-forming effect may be reduced.

(2) Organic Solvent

Various organic solvents typically used in a lithium electrolyte may be used as the organic solvent without limitation. For example, the organic solvent may include a cyclic carbonate-based organic solvent, a linear carbonate-based organic solvent, or a mixed organic solvent thereof.

The cyclic carbonate-based organic solvent is an organic solvent which may well dissociate the lithium salt in the electrolyte due to high permittivity as a highly viscous organic solvent, wherein specific examples of the cyclic carbonate-based organic solvent may be at least one organic solvent selected from ethylene carbonate (EC), propylene carbonate (PC), 1,2-butylene carbonate, 2,3-butylene carbonate, 1,2-pentylene carbonate, 2,3-pentylene carbonate, and vinylene carbonate, and, among them, the cyclic carbonate-based organic solvent may include ethylene carbonate.

Also, the linear carbonate-based organic solvent is an organic solvent having low viscosity and low permittivity, wherein typical examples of the linear carbonate-based organic solvent may be at least one organic solvent selected from dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include ethyl methyl carbonate (EMC).

In order to prepare an electrolyte solution having high ionic conductivity, the organic solvent may include the cyclic carbonate-based organic solvent and the linear carbonate-based organic solvent in a volume ratio of 1:9 to 5:5, for example, 2:8 to 4:6.

Furthermore, the organic solvent may further include a linear ester-based organic solvent and/or a cyclic ester-based organic solvent, which are typically used in an electrolyte solution for a lithium secondary battery, in the cyclic carbonate-based organic solvent and/or the linear carbonate-based organic solvent, if necessary.

As a specific example, the linear ester-based organic solvent may include at least one organic solvent selected from methyl acetate, ethyl acetate, propyl acetate, methyl propionate, ethyl propionate, propyl propionate, and butyl propionate.

As a specific example, the cyclic ester-based organic solvent may include at least one organic solvent selected from γ-butyrolactone, γ-valerolactone, γ-caprolactone, δ-valerolactone, and ε-caprolactone.

The organic solvent may be used by further mixing an ether-based organic solvent or a nitrile-based organic solvent, if necessary, in addition to the carbonate-based organic solvent or the ester-based organic solvent.

Any one selected from the group consisting of dimethyl ether, diethyl ether, dipropyl ether, methylethyl ether, methylpropyl ether, and ethylpropyl ether or a mixture of two or more thereof may be used as the ether-based solvent.

The nitrile-based solvent may include at least one selected from acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

(3) First Additive

The non-aqueous electrolyte solution of the present invention includes a compound represented by the following Formula 1 as a first additive.

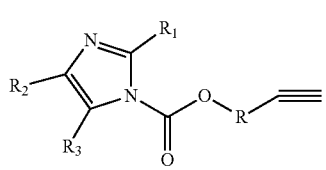

[Formula 1]

In Formula 1,
R is a substituted or unsubstituted alkylene group having 1 to 3 carbon atoms, and
$R_1$ to $R_3$ are each independently hydrogen, an alkyl group having 1 to 3 carbon atoms, or a nitrile group.

In Formula 1, R may be a substituted or unsubstituted alkylene group having 1 or 2 carbon atoms, and $R_1$ to $R_3$ may be each independently hydrogen; or an alkyl group having 1 or 2 carbon atoms.

Specifically, in Formula 1, R may be a substituted or unsubstituted alkylene group having 1 or 2 carbon atoms, and $R_1$ to $R_3$ may be each hydrogen.

More specifically, the compound represented by Formula 1 may be a compound represented by Formula 1a below.

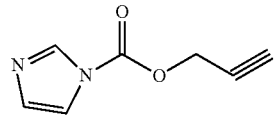

[Formula 1a]

The first additive may be included in an amount of 0.01 wt % to 5 wt %, for example, 0.5 wt % to 3 wt % based on a total weight of the non-aqueous electrolyte solution.

In a case in which the amount of the compound represented by Formula 1 satisfies the above range, since an effect of scavenging a decomposition product of the lithium salt is excellent while suppressing disadvantages, such as a side reaction due to the additive, a decrease in capacity, and an increase in resistance, as much as possible, a secondary battery having more improved overall performance may be prepared.

If the amount of the first additive is less than 0.01 wt %, HF or $PF_5$ may be scavenged, but the scavenging effect may be insignificant over time. Also, if the amount of the first additive is greater than 5.0 wt %, since the viscosity of the non-aqueous electrolyte solution may not only be increased due to the excessive amount of the additive, but ionic conductivity may also be reduced due to the increase in the viscosity to adversely affect mobility of ions in the battery, rate capability or low-temperature life characteristics may be degraded during high-temperature storage.

The non-aqueous electrolyte solution of the present invention may scavenge a Lewis acid, such as HF and $PF_5$, as a decomposition product formed due to the decomposition of anions, in the electrolyte solution by including a compound containing a functional group, which functions as a Lewis base by including a nitrogen element in its structure, like the compound represented by Formula 1. Thus, since a degradation behavior due to a chemical reaction of the film on the surface of the positive electrode or negative electrode, which is caused by the Lewis acid, may be suppressed, additional electrolyte solution decomposition of the battery due to the destruction or degradation of the film may be prevented, and, furthermore, high-temperature storage characteristics may be improved by mitigating self-discharge of the secondary battery.

Particularly, since the compound represented by Formula 1 has a propargyl functional group in its structure, a SEI having high passivation ability is formed on the surface of the negative electrode while the functional group is reduction-decomposed, and thus, high-temperature durability of the negative electrode itself may not only be improved, but electrodeposition of transition metals on the surface of the negative electrode may also be prevented. Also, the compound represented by Formula 1 may function to make the dissolution of impurities difficult to occur by being adsorbed on the surface of the metallic impurities included in the positive electrode due to the propargyl group, and, accordingly, an internal short circuit, which may occur by precipitation of the dissolved metal ions on the negative electrode, may be suppressed. Furthermore, since the propargyl group is easily reduced on the surface of the negative electrode, it may form a stable film on the surface of the negative electrode, and thus, a self-discharge reaction of the graphite-based, silicon-based negative electrode due to an additional reduction decomposition reaction of the electrolyte solution caused by instability of the SEI may be prevented.

Also, in addition to the metal ion adsorption and the formation of the SEI, the compound represented by Formula 1 suppresses the formation of HF due to the decomposition of the lithium salt because a unshared electron pair of nitrogen (N) stabilizes the anions of the lithium salt, and thus, high-temperature storage characteristics of the secondary battery may be further improved.

Thus, since the non-aqueous electrolyte solution including the compound represented by Formula 1 of the present invention may suppress the dissolution of metal into ions by being adsorbed on the surface of the metal, it may not only suppress the occurrence of the internal short circuit, but also may stably form a SEI and may prevent the destruction of the positive/negative film by the decomposition of the lithium salt, and thus, high-temperature durability may be improved by suppressing the self-discharge reaction of the lithium secondary battery.

(4) Second Additive

Also, the non-aqueous electrolyte solution of the present invention further includes lithium difluorophosphate (LiDFP) represented by the following Formula 2 as a second additive.

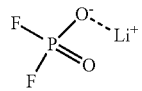

[Formula 2]

The lithium difluorophosphate (LiDFP) is a component for achieving an effect of improving long-term life characteristics of the secondary battery, wherein a lithium ion component formed by decomposition during initial charge is electrochemically decomposed on the surface of the negative electrode to form a stable SEI. The formation of the SEI may not only improve lithium (Li) mobility toward the negative electrode, but may also reduce interfacial resistance. Also, difluorophosphate anions formed by decomposition during initial charge may improve stabilization of the positive electrode and discharge characteristics while being present on the surface of the positive electrode. Thus, the effect of improving long-term life characteristics of the secondary battery may be achieved.

In the non-aqueous electrolyte solution of the present invention, the first additive and the second additive may be included in a weight ratio of 1:2 to 1:10, for example, 1:2 to 1:5.

In a case in which the first additive and the second additive are mixed in the above ratio, wetting of the electrolyte solution may be improved by reducing surface tension. Also, a side reaction between the electrode and the electrolyte solution may be suppressed during charge at high temperatures by forming a stable SEI without an increase in resistance.

If, in a case in which the weight ratio of the second additive to the first additive is greater than 10, since initial interfacial resistance is increased while an excessively thick film is formed on the surface of the electrode, output may be reduced. Also, in a case in which the weight ratio of the second additive to the first additive is less than 1, since an SEI-forming effect is insignificant, an effect of suppressing the side reaction between the electrode and the electrolyte solution may be reduced.

(5) Third Additive (Additional Additives)

Also, in order to prevent the non-aqueous electrolyte solution from being decomposed to cause collapse of the negative electrode in a high-output environment, or further improve low-temperature high-rate discharge characteristics, high-temperature stability, overcharge protection, and a battery swelling suppression effect at high temperatures, the non-aqueous electrolyte solution for a lithium secondary battery of the present invention may further include additional third additives in the non-aqueous electrolyte solution, if necessary.

The non-aqueous electrolyte solution for a lithium secondary battery may further include at least one third additive selected from among a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, and a lithium salt-based compound.

Examples of the cyclic carbonate-based compound may be vinylene carbonate (VC) or vinyl ethylene carbonate.

An example of the halogen-substituted carbonate-based compound may be fluoroethylene carbonate (FEC).

Examples of the sultone-based compound may be at least one compound selected from 1,3-propane sultone (PS), 1,4-butane sultone, ethane sultone, 1,3-propene sultone (PRS), 1,4-butene sultone, and 1-methyl-1,3-propene sultone.

Examples of the sulfate-based compound may be ethylene sulfate (Esa), trimethylene sulfate (TMS), and methyl trimethylene sulfate (MTMS).

Examples of the phosphate-based compound may be at least one compound selected from lithium difluorobis(oxalato)phosphate, tetramethyltrimethylsilyl phosphate, trimethylsilyl phosphite, tris(2,2,2-trifluoroethyl)phosphate, and tris(trifluoroethyl)phosphite, in addition to the lithium difluorophosphate included as the second additive.

Examples of the borate-based compound may be tetraphenylborate and lithium oxalyldifluoroborate.

Examples of the nitrile-based compound may be at least one compound selected from succinonitrile, adiponitrile, acetonitrile, propionitrile, butyronitrile, valeronitrile, caprylonitrile, heptanenitrile, cyclopentanecarbonitrile, cyclohexanecarbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

An example of the benzene-based compound may be fluorobenzene, examples of the amine-based compound may be triethanolamine and ethylenediamine, and an example of the silane-based compound may be tetravinylsilane.

The lithium salt-based compound is a compound different from the lithium salt included in the non-aqueous electrolyte solution, wherein examples of the lithium salt-based compound may be at least one compound selected from the group consisting of $LiPO_2F_2$, LiODFB, LiBOB (lithium bis(oxalato)borate ($LiB(C_2O_4)_2$)), and $LiBF_4$.

In a case in which, among these third additives, vinylene carbonate, vinyl ethylene carbonate, or succinonitrile is included, a more robust SEI may be formed on the surface of the negative electrode during an initial activation process of the secondary battery.

In a case in which the $LiBF_4$ is included, high-temperature stability of the secondary battery may be improved by suppressing generation of a gas which may be generated due to the decomposition of the electrolyte solution at high temperatures.

The third additive may be used as a mixture of two or more thereof, and may be included in an amount of 0.01 wt % to 50 wt %, particularly 0.01 wt % to 10 wt %, and preferably 0.05 wt % to 5 wt % based on the total weight of the non-aqueous electrolyte solution. If the amount of the third additive is less than 0.01 wt %, effects of improving low-temperature output, high-temperature storage characteristics, and high-temperature life characteristics of the battery are insignificant, and, if the amount of the third additive is greater than 50 wt %, there is a possibility that the side reaction in the electrolyte solution occurs excessively during charge and discharge of the battery. Particularly, since the third additive may not be sufficiently decomposed at high temperatures when an excessive amount of the third additive is added, the third additive may be present in the form of an unreacted material or precipitates in the electrolyte solution at room temperature. Accordingly, a side reaction may occur in which life or resistance characteristics of the secondary battery are degraded.

Lithium Secondary Battery

Also, in another embodiment of the present invention, there is provided a lithium secondary battery including the non-aqueous electrolyte solution for a lithium secondary battery of the present invention.

The lithium secondary battery of the present invention may be prepared by forming an electrode assembly, in which a positive electrode, a negative electrode, and a separator disposed between the positive electrode and the negative electrode are sequentially stacked, accommodating the electrode assembly in a battery case, and then injecting the non-aqueous electrolyte solution of the present invention.

A typical method known in the art may be used as a method of preparing the lithium secondary battery of the present invention, and, specifically, the method of preparing the lithium secondary battery of the present invention is as described below.

(1) Positive Electrode

The positive electrode may be prepared by coating a positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel; aluminum; nickel; titanium; fired carbon; or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include a lithium transition metal oxide including lithium and at least one metal selected from cobalt, manganese, nickel, or aluminum, and may specifically include at least one selected from lithium-manganese-based oxide with high stability and capacity characteristics of the battery, lithium iron phosphate, and lithium-nickel-manganese-cobalt-based oxide (e.g., $Li(Ni_pCo_qMn_{r1})O_2$ (where $0<p<1$, $0<q<1$, $0<r1<1$, and $p+q+r1=1$).

Specifically, the lithium-manganese-based oxide may, for example, include $LiMn_2O_4$, and the lithium iron phosphate may, for example, include $LiFePO_4$.

Also, the lithium-nickel-manganese-cobalt-based oxide may include at least one selected from $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, and $Li(Ni_{0.8}Mn_{0.1}Co_{0.1})O_2$, wherein, among them, the lithium-nickel-manganese-cobalt-based oxide may include a lithium transition metal oxide in which an amount of nickel among transition metals is 60 atm % or more. That is, since the higher the amount of the nickel among the transition metals is the higher the capacity may be achieved, it is more advantageous in using the lithium transition metal oxide having a nickel content of 0.6 or more to achieve high capacity. Specifically, the lithium transition metal oxide may include at least one selected from $Li(Ni_{0.6}Mn_{0.2}Co_{0.2})O_2$, $Li(Ni_{0.7}Mn_{0.15}Co_{0.15})O_2$, and $Li(Ni_{0.8}Mn_{0.1}Co_{0.1})O_2$.

In addition to the above lithium transition metal oxide, the positive electrode active material of the present invention may further include at least one lithium transition metal oxide selected from lithium-cobalt-based oxide such as $LiCoO_2$; lithium-nickel-based oxide such as $LiNiO_2$; lithium-nickel-manganese-based oxide such as $LiNi_{1-Y}Mn_YO_2$ (where $0<Y<1$) and $LiMn_{2-Z}Ni_ZO_4$ (where $0<Z<2$); lithium-nickel-cobalt-based oxide such as $LiNi_{1-Y1}Co_{Y1}O_2$ (where $0<Y1<1$); lithium-manganese-cobalt-based oxide such as $LiCo_{1-Y2}Mn_{Y2}O_2$ (where $0<Y2<1$) and $LiMn_{2-Z1}Co_{Z1}O_4$ (where $0<Z1<2$); lithium-nickel-manganese-cobalt-based oxide such as $Li(Ni_pCo_qMn_{r1})O_2$ (where $0<p<1$, $0<q<1$, $0<r1<1$, and $p+q+r1=1$) and $Li(Ni_{p1}Co_{q1}Mn_{r2})O_4$ (where $0<p1<2$, $0<q1<2$, $0<r2<2$, and $p1+q1+r2=2$); and lithium-nickel-cobalt-transition metal (M) oxide such as $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$).

The positive electrode active material may be included in an amount of 80 wt % to 99 wt %, for example, 90 wt % to 99 wt % based on a total weight of solid content in the positive electrode slurry. In a case in which the amount of the positive electrode active material is 80 wt % or less, since energy density is reduced, capacity may be reduced.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene termonomer, a styrene-butadiene rubber, and a fluoro rubber.

Also, the conductive agent is a material providing conductivity without causing adverse chemical changes in the battery, wherein it may be added in an amount of 1 wt % to 20 wt % based on the total weight of the solid content in the positive electrode slurry.

As a typical example of the conductive agent, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

Furthermore, the solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 60 wt %, for example, 20 wt % to 50 wt %.

(2) Negative Electrode

The negative electrode may be prepared by coating a negative electrode collector with a negative electrode slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper; stainless steel; aluminum; nickel; titanium; fired carbon; copper or stainless steel that is surface-treated with one of carbon, nickel, titanium, silver, or the like; and an aluminum-cadmium alloy may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include compounds capable of reversibly intercalating/deintercalating lithium ions, and, for example, may include a carbon-based active material, a silicon-based active material, or a mixture thereof.

As the carbon-based active material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

Also, the silicon-based active material, which may be doped and undoped with lithium, may include silicon (Si), $SiO_x$ ($0<x\leq2$), a Si—Y alloy (where Y is an element selected from the group consisting of alkali metal, alkaline earth metal, a Group 13 element, a Group 14 element, transition metal, a rare earth element, and a combination thereof, and is not Si), and a mixture of $SiO_2$ and at least one thereof may also be used. The element Y may be selected from the group consisting of Mg, calcium (Ca), strontium (Sr), barium (Ba), radium (Ra), scandium (Sc), yttrium (Y), Ti, zirconium (Zr), hafnium (Hf), rutherfordium (Rf), V, niobium (Nb), Ta, dubnium (Db), Cr, Mo, tungsten (W), seaborgium (Sg), technetium (Tc), rhenium (Re), bohrium (Bh), Fe, lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), Al, gallium (Ga), tin (Sn), indium (In), germanium (Ge), phosphorus (P), arsenic (As), antimony (Sb), bismuth (Bi), sulfur (S), selenium (Se), tellurium (Te), polonium (Po), and a combination thereof.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene monomer, a styrene-butadiene rubber, and a fluoro rubber.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content in the slurry including the negative electrode active material as well as selectively the binder and the conductive agent is in a range of 50 wt % to 75 wt %, for example, 50 wt % to 65 wt %.

(3) Separator

A typical porous polymer film generally used, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator included in the lithium secondary battery of the present invention, and a typical porous nonwoven fabric, for example, a nonwoven fabric formed of high melting point glass fibers or polyethylene terephthalate fibers may be used, but the present invention is not limited thereto.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Preparation of Non-aqueous Electrolyte Solution for Lithium Secondary Battery)

A non-aqueous electrolyte solution for a lithium secondary battery was prepared by adding 0.5 g of the compound represented by Formula 1a as a first additive, 1.0 g of lithium difluorophosphate as a second additive, and 0.1 g of tetravinyl silane, 1.0 g of ethylene sulfonate, 0.5 g of 1,3-propane sultone, 0.2 g of $LiBF_4$, and 6.0 g of fluorobenzene, as a third additive, to 90.7 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$:$Li(Ni_{0.6}Co_{0.2}Mn_{0.2})O_2$=7:3 weight ratio), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Example 2

(Preparation of Non-aqueous Electrolyte Solution for Lithium Secondary Battery)

A non-aqueous electrolyte solution for a lithium secondary battery was prepared by adding 0.2 g of the compound represented by Formula 1a as a first additive, 1.0 g of lithium difluorophosphate as a second additive, and 1.0 g of ethylene sulfonate, 0.5 g of 1,3-propane sultone, 0.2 g of $LiBF_4$, and 6.0 g of fluorobenzene, as a third additive, to 91.1 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Example 3

(Preparation of Non-aqueous Electrolyte Solution for Lithium Secondary Battery)

A non-aqueous electrolyte solution for a lithium secondary battery was prepared by adding 0.5 g of the compound represented by Formula 1a as a first additive, 1.0 g of lithium difluorophosphate as a second additive, and 0.1 g of tetravinyl silane, 1.0 g of ethylene sulfonate, 0.5 g of 1,3-propane sultone, 0.2 g of $LiBF_4$, and 6.0 g of fluorobenzene, as a third additive, to 90.7 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Example 4

(Preparation of Non-aqueous Electrolyte Solution for Lithium Secondary Battery)

A non-aqueous electrolyte solution for a lithium secondary battery was prepared by adding 0.3 g of the compound represented by Formula 1a as a first additive, 1.0 g of lithium difluorophosphate as a second additive, and 1.0 g of ethylene sulfonate, 0.5 g of 1,3-propane sultone, 0.2 g of $LiBF_4$, and 6.0 g of fluorobenzene, as a third additive, to 91.0 g of an organic solvent (ethylene carbonate:ethyl methyl carbonate=3:7 volume ratio) in which 1.2 M $LiPF_6$ was dissolved.

(Secondary Battery Preparation)

A positive electrode active material ($Li(Ni_{0.8}Co_{0.1}Mn_{0.1})O_2$), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Example 5

(Preparation of Non-aqueous Electrolyte Solution for Lithium Secondary Battery)

A non-aqueous electrolyte solution for a lithium secondary battery was prepared by adding 0.1 g of the compound represented by Formula 1a as a first additive, 1.0 g of lithium difluorophosphate as a second additive, and 1.0 g of ethylene sulfonate, 0.5 g of 1,3-propane sultone, and 0.2 g of $LiBF_4$, as a third additive, to 97.2 g of an organic solvent (ethylene carbonate:ethyl methyl carbonate=3:7 volume ratio) in which 1.2 M $LiPF_6$ was dissolved.

(Secondary Battery Preparation)

A lithium secondary battery was prepared in the same manner as in Example 4 except that the above-prepared non-aqueous electrolyte solution for a lithium secondary battery, instead of the non-aqueous electrolyte solution for a lithium secondary battery of Example 4, was used.

Example 6

(Preparation of Non-aqueous Electrolyte Solution for Lithium Secondary Battery)

A non-aqueous electrolyte solution for a lithium secondary battery was prepared by adding 0.3 g of the compound represented by Formula 1a as a first additive, 1.5 g of lithium difluorophosphate as a second additive, and 0.1 g of tetravinyl silane (TVS), 1.0 g of ethylene sulfonate, 0.5 g of 1,3-propane sultone, and 0.2 g of $LiBF_4$, as a third additive, to 96.4 g of an organic solvent (ethylene carbonate:ethyl methyl carbonate=3:7 volume ratio) in which 1.2 M $LiPF_6$ was dissolved.

(Secondary Battery Preparation)

A lithium secondary battery was prepared in the same manner as in Example 4 except that the above-prepared non-aqueous electrolyte solution for a lithium secondary battery, instead of the non-aqueous electrolyte solution for a lithium secondary battery of Example 4, was used.

COMPARATIVE EXAMPLES

Comparative Example 1

(Preparation of Non-aqueous Electrolyte Solution for Lithium Secondary Battery)

A non-aqueous electrolyte solution for a lithium secondary battery was prepared by adding 1.0 g of lithium difluorophosphate, as a second additive, and 0.1 g of tetravinyl silane, 1.0 g of ethylene sulfonate, 0.5 g of 1,3-propane sultone, 0.2 g of $LiBF_4$, and 6.0 g of fluorobenzene, as a third additive, to 91.2 g of an organic solvent (ethylene carbonate: ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$:$Li(Ni_{0.6}Co_{0.2}Mn_{0.2})O_2$=7:3 weight ratio), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Comparative Example 2

(Preparation of Non-aqueous Electrolyte Solution for Lithium Secondary Battery)

A non-aqueous electrolyte solution for a lithium secondary battery was prepared by adding 1.0 g of lithium difluorophosphate, as a second additive, and 0.1 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 91.2 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Comparative Example 3

(Preparation of Non-aqueous Electrolyte Solution for Lithium Secondary Battery)

A non-aqueous electrolyte solution for a lithium secondary battery was prepared by adding 0.3 g of a compound of the following Formula 3, 1.0 g of lithium difluorophosphate, as a second additive, and 0.1 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 90.9 g of an organic solvent (ethylene carbonate:ethyl methyl carbonate=3:7 volume ratio) in which 1.2 M $LiPF_6$ was dissolved.

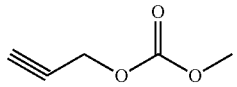

[Formula 3]

(Secondary Battery Preparation)

A lithium secondary battery was prepared in the same manner as in Example 4 except that the above-prepared non-aqueous electrolyte solution for a lithium secondary battery, instead of the non-aqueous electrolyte solution for a lithium secondary battery of Example 4, was used.

Comparative Example 4

(Preparation of Non-aqueous Electrolyte Solution for Lithium Secondary Battery)

A non-aqueous electrolyte solution for a lithium secondary battery was prepared by adding 1.0 g of lithium difluorophosphate, as a second additive, and 0.1 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 91.2 g of an organic solvent (ethylene carbonate:ethyl methyl carbonate=3:7 volume ratio) in which 1.2 M $LiPF_6$ was dissolved.

(Secondary Battery Preparation)

A lithium secondary battery was prepared in the same manner as in Comparative Example 3 except that the above-prepared non-aqueous electrolyte solution for a lithium secondary battery, instead of the non-aqueous electrolyte solution for a lithium secondary battery of Comparative Example 3, was used.

Comparative Example 5

(Preparation of Non-aqueous Electrolyte Solution for Lithium Secondary Battery)

A non-aqueous electrolyte solution for a lithium secondary battery was prepared by adding 1.0 g of lithium difluorophosphate, as a second additive, and 0.1 g of tetravinyl silane (TVS), 1.0 g of ethylene sulfonate, 0.5 g of 1,3-propane sultone, and 0.2 g of $LiBF_4$, as a third additive, to 97.2 g of an organic solvent (ethylene carbonate:ethyl methyl carbonate=3:7 volume ratio) in which 1.2 M $LiPF_6$ was dissolved.

(Secondary Battery Preparation)

A secondary battery was prepared in the same manner as in Comparative Example 3 except that the above-prepared non-aqueous electrolyte solution for a lithium secondary battery, instead of the non-aqueous electrolyte solution for a lithium secondary battery of Comparative Example 3, was used.

Comparative Example 6

(Preparation of Non-aqueous Electrolyte Solution for Lithium Secondary Battery)

A non-aqueous electrolyte solution for a lithium secondary battery was prepared by adding 1.5 g of lithium difluorophosphate, as a second additive, and 0.1 g of tetravinyl silane (TVS), 1.0 g of ethylene sulfonate, 0.5 g of 1,3-propane sultone, and 0.2 g of $LiBF_4$, as a third additive, to 96.8 g of an organic solvent (ethylene carbonate:ethyl methyl carbonate=3:7 volume ratio) in which 1.2 M $LiPF_6$ was dissolved.

(Secondary Battery Preparation)

A secondary battery was prepared in the same manner as in Comparative Example 3 except that the above-prepared non-aqueous electrolyte solution for a lithium secondary battery, instead of the non-aqueous electrolyte solution for a lithium secondary battery of Comparative Example 3, was used.

Comparative Example 7

(Preparation of Non-aqueous Electrolyte Solution for Lithium Secondary Battery)

A non-aqueous electrolyte solution for a lithium secondary battery was prepared by adding 1.0 g of lithium difluorophosphate, as a second additive, and 0.2 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 91.1 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A positive electrode active material ($Li(Ni_{0.8}Co_{0.1}Mn_{0.1})O_2$), carbon black as a conductive agent, and polyvinylidene fluoride, as a binder, were added to N-methyl-2-pyrrolidone (NMP), as a solvent, at a weight ratio of 97.5:1:1.5 to prepare a positive electrode slurry (solid content: 50 wt %). A 15 μm thick positive electrode collector (Al thin film) was coated with the positive electrode slurry, dried, and then roll-pressed to prepare a positive electrode.

A negative electrode active material (graphite:SiO=95:5 weight ratio), a binder (SBR-CMC), and a conductive agent (carbon black) were added in a weight ratio of 95:3.5:1.5 to water, as a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly prepared was accommodated in a battery case, and the non-aqueous electrolyte solution for a lithium secondary battery was injected thereinto to prepare a lithium secondary battery.

Comparative Example 8

(Preparation of Non-aqueous Electrolyte Solution for Lithium Secondary Battery)

A non-aqueous electrolyte solution for a lithium secondary battery was prepared by adding 1.0 g of the compound represented by Formula 1a as a first additive, 1.0 g of lithium difluorophosphate as a second additive, and 0.2 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 90.1 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A secondary battery was prepared in the same manner as in Comparative Example 7 except that the above-prepared non-aqueous electrolyte solution for a lithium secondary battery, instead of the non-aqueous electrolyte solution for a lithium secondary battery of Comparative Example 7, was used.

Comparative Example 9

(Preparation of Non-aqueous Electrolyte Solution for Lithium Secondary Battery)

A non-aqueous electrolyte solution for a lithium secondary battery was prepared by adding 0.08 g of the compound represented by Formula 1a as a first additive, 1.0 g of lithium difluorophosphate as a second additive, and 0.2 g of tetravinyl silane (TVS), 1.0 g of ethylene sulfonate, 0.5 g of 1,3-propane sultone, 0.2 g of $LiBF_4$, and 6.0 g of fluorobenzene, as a third additive, to 91.02 g of an organic solvent (ethylene carbonate:ethyl methyl carbonate=3:7 volume ratio) in which 0.7 M $LiPF_6$ and 0.3 M LiFSI were dissolved.

(Secondary Battery Preparation)

A secondary battery was prepared in the same manner as in Comparative Example 7 except that the above-prepared non-aqueous electrolyte solution for a lithium secondary battery, instead of the non-aqueous electrolyte solution for a lithium secondary battery of Comparative Example 7, was used.

The first additives and second additives used in the examples and the comparative examples were summarized and listed in Table 1 below.

TABLE 1

|  | First additive | | Second additive | | First additive:second additive |
| --- | --- | --- | --- | --- | --- |
|  | Type | Amount (g) | Type | Amount (g) | Weight ratio |
| Example 1 | Formula 1a | 0.5 | LiDFP | 1.0 | 1:2 |
| Example 2 | Formula 1a | 0.2 | LiDFP | 1.0 | 1:5 |
| Example 3 | Formula 1a | 0.5 | LiDFP | 1.0 | 1:2 |
| Example 4 | Formula 1a | 0.3 | LiDFP | 1.0 | 1:3.3 |
| Example 5 | Formula 1a | 0.1 | LiDFP | 1.0 | 1:10 |
| Example 6 | Formula 1a | 0.3 | LiDFP | 1.5 | 1:5 |
| Comparative Example 1 | — | — | LiDFP | 1.0 | — |
| Comparative Example 2 | — | — | LiDFP | 1.0 | — |
| Comparative Example 3 | Formula 3 (not included in Formula 1) | 0.3 | LiDFP | 1.0 | 1:3.3 |
| Comparative Example 4 | — | — | LiDFP | 1.0 | — |
| Comparative Example 5 | — | — | LiDFP | 1.0 | — |
| Comparative Example 6 | — | — | LiDFP | 1.5 | — |
| Comparative Example 7 | — | — | LiDFP | 1.0 | — |
| Comparative Example 8 | Formula 1a | 1.0 | LiDFP | 1.0 | 1:1 |
| Comparative Example 9 | Formula 1a | 0.08 | LiDFP | 1.0 | 1:12.5 |

EXPERIMENTAL EXAMPLES

Experimental Example 1-1: High-temperature (60° C.) Storage Durability Evaluation (1)

After each of the lithium secondary batteries prepared in Example 1 and Comparative Example 1 was activated at a CC of 0.1 C, degassing was performed.

Subsequently, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Subsequently, each lithium secondary battery was recharged at 0.33 C rate under a constant current condition to a state of charge (SOC) of 100% and then stored at a high temperature (60° C.) for 13 weeks.

After charge and discharge were performed in which, after every 2 weeks, 4 weeks, 8 weeks, 10 weeks, and 13 weeks, each lithium secondary battery was charged at 0.33 C rate to 4.20 V under a constant current-constant voltage (CC-CV) charging condition and then discharged at 0.33 C rate under a constant current condition to 2.5 V, discharge capacity after high-temperature storage was measured using PNE-0506 charge/discharge equipment (manufacturer: PNE SOLUTION Co., Ltd., 5 V, 6 A).

Also, after every 2 weeks, 4 weeks, 8 weeks, 10 weeks, and 13 weeks, each lithium secondary battery was charged to a state of charge (SOC) of 50%, and resistance (DC-iR) after high-temperature storage was then calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

The calculated initial resistance and the resistance after high-temperature storage measured every week were substituted into the following [Equation 1] to calculate a resistance increase rate (%), and the results thereof are then presented in FIG. 1.

$$\text{Resistance increase rate (\%)} = \{(\text{resistance after high-temperature storage} - \text{initial resistance})/\text{initial resistance}\} \times 100 \quad [\text{Equation 1}]$$

Furthermore, the initial discharge capacity measured and the discharge capacity after high-temperature storage measured every week were substituted into the following [Equation 2] to calculate a capacity retention (%), and the results thereof are then presented in FIG. 1.

$$\text{Capacity retention (\%)} = (\text{discharge capacity after high-temperature storage}/\text{initial discharge capacity}) \times 100 \quad [\text{Equation 2}]$$

Referring to FIG. 1, it may be understood that a capacity retention (%) and a resistance increase rate (%) after high-temperature storage of the secondary battery of Example 1 were improved in comparison to those of Comparative Example 1.

Experimental Example 1-2: High-temperature (60° C.) Storage Durability Evaluation (2)

After each of the secondary batteries prepared in Examples 2 and 3 and the lithium secondary batteries prepared in Comparative Examples 2 and 3 was activated at a CC of 0.1 C, degassing was performed.

Subsequently, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Subsequently, each lithium secondary battery was recharged at 0.33 C rate under a constant current condition to a state of charge (SOC) of 100% and then stored at a high temperature (60° C.) for 2 weeks.

After CC-CV charge and discharge were performed at a CC of 0.33 C after 2 weeks, discharge capacity after high-temperature storage was measured using PNE-0506 charge/discharge equipment (manufacturer: PNE SOLUTION Co., Ltd., 5 V, 6 A). Then, after each lithium secondary battery was charged to a state of charge (SOC) of 50%, resistance (DC-iR) after high-temperature storage was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

The calculated initial resistance and the resistance after high-temperature storage were substituted into [Equation 1] to calculate a resistance increase rate (%), and the results thereof are then presented in Table 2 below.

Furthermore, the initial discharge capacity measured and the discharge capacity after high-temperature storage measured after 2 weeks were substituted into [Equation 2] to calculate a capacity retention (%), and the results thereof are then presented in Table 2 below.

TABLE 2

| | After 2 weeks of high-temperature (60° C.) storage | |
|---|---|---|
| | Capacity retention (%) | Resistance increase rate (%) |
| Example 2 | 92.20 | 2.71 |
| Example 3 | 92.09 | 1.65 |
| Comparative Example 2 | 91.49 | 5.69 |
| Comparative Example 3 | 91.89 | 3.19 |

Referring to Table 2, it may be understood that capacity retentions and resistance increase rates after high-temperature storage of the secondary batteries of Examples 2 and 3 were significantly improved in comparison to those of Comparative Examples 2 and 3, respectively.

Experimental Example 1-3: High-temperature (60° C.) Storage Durability Evaluation (3)

After each of the secondary batteries prepared in Examples 4 and 6 and the lithium secondary batteries prepared in Comparative Examples 4 to 6 was activated at a CC of 0.1 C, degassing was performed.

Thereafter, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Next, each lithium secondary battery was recharged at a CC of 0.33 C to a state of charge (SOC) of 100% and then stored at a high temperature (60° C.) for 2 weeks.

After CC-CV charge and discharge were performed at a CC of 0.33 C after 2 weeks, discharge capacity after high-temperature storage was measured using PNE-0506 charge/discharge equipment (manufacturer: PNE SOLUTION Co., Ltd., 5 V, 6 A). Also, after each lithium secondary battery was charged to a state of charge (SOC) of 50%, resistance (DC-iR) after high-temperature storage was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

The calculated initial resistance and the resistance after high-temperature storage were substituted into [Equation 1] to calculate a resistance increase rate (%), and the results thereof are then presented in Table 3 below.

Furthermore, the measured initial discharge capacity and the discharge capacity after storage measured after 2 weeks were substituted into [Equation 2] to calculate a capacity retention (%), and the results thereof are then presented in Table 3 below.

TABLE 3

| | After 2 weeks of high-temperature (60° C.) storage | |
|---|---|---|
| | Capacity retention (%) | Resistance increase rate (%) |
| Example 4 | 100.16 | −3.33 |
| Example 6 | 99.06 | −4.21 |
| Comparative Example 4 | 99 | 1.06 |
| Comparative Example 5 | 98.85 | −2.70 |
| Comparative Example 6 | 98.63 | −2.26 |

Referring to Table 3, it may be understood that capacity retentions and resistance increase rates after high-temperature storage of the secondary batteries of Examples 4 and 6 were improved in comparison to those of Comparative Examples 4 to 6, respectively.

Experimental Example 1-4: High-temperature (60° C.) Storage Durability Evaluation (4)

After each of the secondary battery prepared in Example 1 and the lithium secondary batteries prepared in Comparative Examples 7 to 9 was activated at a CC of 0.1 C, degassing was performed.

Thereafter, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50% based on the measured discharge capacity, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Next, each lithium secondary battery was recharged at a CC of 0.33 C to a state of charge (SOC) of 100% and then stored at a high temperature (60° C.) for 7 weeks.

After CC-CV charge and discharge were performed at a CC of 0.33 C after 7 weeks, discharge capacity after high-temperature storage was measured using PNE-0506 charge/discharge equipment (manufacturer: PNE SOLUTION Co., Ltd., 5 V, 6 A). Also, after each lithium secondary battery was charged to a state of charge (SOC) of 50% based on the measured discharge capacity, resistance (DC-iR) after high-temperature storage was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

The resistance after high-temperature storage was presented in Table 4 below.

TABLE 4

| | After 7 weeks storage at high-temperature (60° C.) Resistance (mohm) |
|---|---|
| Example 1 | 43 |
| Comparative Example 7 | 48 |
| Comparative Example 8 | 63 |
| Comparative Example 9 | 70 |

According to the results of Table 4, in a case in which the weight ratio of the first additive to the second additive was deviated from 1:2 to 1:10 and became 1:1 (Comparative Example 8) or 1:12.5 (Comparative Example 9), it may be confirmed that resistance values after high-temperature storage were even higher than that of a case (Comparative Example 7) where the first additive was not included. That is, it may be understood that that the weight ratio of the first additive to the second additive is in a range of 1:2 to 1:10 is an essential condition for improving a high-temperature output retention.

Experimental Example 2-1: High-temperature (45° C.) Life Characteristics Evaluation (1)

After each of the lithium secondary battery prepared in Example 1 and the secondary battery prepared in Comparative Example 1 was activated at a CC of 0.1 C, degassing was performed.

Subsequently, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Subsequently, each lithium secondary battery was charged at a CC of 0.33 C to 4.20 V under a constant current-constant voltage (CC-CV) charging condition at 45° C., then subjected to 0.05 C current cut-off, and discharged at a CC of 0.33 C to 2.5 V. The above charging and discharging were defined as one cycle, and 200 cycles of charging and discharging were performed at a high temperature (45° C.)

Each lithium secondary battery was charged at a CC of 0.33 C, then subjected to 0.05 C current cut-off, and then discharged at a CC of 0.33 C to 2.5 V to measure discharge capacity every 50 cycles at 25° C. using PNE-0506 charge/discharge equipment (manufacturer: PNE SOLUTION Co., Ltd., 5 V, 6 A), this was substituted into the following [Equation 3] to calculate a capacity retention (%), and the results thereof are presented in FIG. 2.

$$\text{Capacity retention (\%)} = \text{(discharge capacity every 50 cycles/initial discharge capacity)} \times 100 \quad \text{[Equation 3]}$$

Also, direct current internal resistance (hereinafter, referred to as "DC-iR") was calculated by a voltage drop obtained in a state in which each lithium secondary battery was subjected to a discharge pulse at 2.5 C for 10 seconds at an SOC of 50%, this was substituted into the following [Equation 4] to calculate a resistance increase rate (%) every 50 cycles, and the results thereof are then presented in FIG. 2. The voltage drop was measured using PNE-0506 charge/discharge equipment (manufacturer: PNE SOLUTION Co., Ltd., 5 V, 6 A).

$$\text{Resistance increase rate (\%)} = \{\text{(resistance after every 50 cycles-initial resistance)/initial resistance}\} \times 100 \quad \text{[Equation 4]}$$

Referring to FIG. 2, the secondary batteries of Example 1 and Comparative Example 1 had an equivalent level of discharge capacity retention after 200 cycles, but it may be understood that a resistance increase rate after 200 cycles of the secondary battery of Comparative Example 1 was significantly degraded in comparison to that of the secondary battery of Example 1.

That is, with respect to the secondary battery of Example 1, since a stable film was formed on the surfaces of the positive electrode/negative electrode, it may be confirmed that the resistance increase rate was improved in comparison to that of Comparative Example 1 due to the suppression of additional electrolyte decomposition when long-term charge and discharge at high temperature were performed.

Experimental Example 2-2: High-temperature (45° C.) Life Characteristics Evaluation (2)

After each of the lithium secondary batteries prepared in Examples 2 and 3 and the secondary battery prepared in Comparative Example 2 was activated at a CC of 0.1 C, degassing was performed.

Subsequently, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Subsequently, each lithium secondary battery was charged at a CC of 0.33 C to 4.20 V under a constant current-constant voltage (CC-CV) charging condition at 45° C., then subjected to 0.05 C current cut-off, and discharged at a CC of 0.33 C to 2.5 V. The above charging and discharging were defined as one cycle, and 50 cycles of charging and discharging were performed at a high temperature (45° C.)

Also, after 50 cycles of charging and discharging were performed, each lithium secondary battery was charged at a CC of 0.33 C, then subjected to 0.05 C current cut-off, and discharged at a CC of 0.33 C to 2.5 V to measure discharge capacity after 50 cycles at 25° C. using PNE-0506 charge/discharge equipment (manufacturer: PNE SOLUTION Co., Ltd., 5 V, 6 A), this was substituted into [Equation 3] to measure a capacity retention, and the results thereof are presented in Table 5 below.

Furthermore, direct current internal resistance (hereinafter, referred to as "DC-iR") was calculated by a voltage drop obtained in a state in which each lithium secondary battery was subjected to a discharge pulse at 2.5 C for 10 seconds at an SOC of 50%, this was substituted into [Equation 4] to calculate a resistance increase rate (%) after 50 cycles, and the results thereof are then presented in Table 5 below. The voltage drop was measured using PNE-0506 charge/discharge equipment (manufacturer: PNE SOLUTION Co., Ltd., 5 V, 6 A).

TABLE 5

| | After 50 cycles at high temperature (45° C.) ||
| | Capacity retention (%) | Resistance increase rate (%) |
|---|---|---|
| Example 2 | 94.20 | 0.94 |
| Example 3 | 93.76 | 1.76 |
| Comparative Example 2 | 93.60 | 4.01 |

Referring to Table 5, with respect to the secondary batteries of Examples 2 and 3, since a stable film was formed on the surfaces of the positive electrode/negative electrode, it may be confirmed that capacity retentions and resistance increase rates were significantly improved in comparison to those of Comparative Example 2 due to the suppression of additional electrolyte decomposition when long-term charge and discharge at high temperature were performed.

Experimental Example 2-3: High-temperature (45° C.) Life Characteristics Evaluation (3)

After each of the lithium secondary battery prepared in Example 5 and the secondary battery prepared in Comparative Example 5 was activated at a CC of 0.1 C, degassing was performed.

Subsequently, each lithium secondary battery was charged at 0.33 C rate to 4.20 V under a constant current-constant voltage (CC-CV) charging condition at 25° C., then subjected to 0.05 C current cut-off, and discharged at 0.33 C rate under a constant current condition to 2.5 V. After the above charging and discharging were defined as one cycle and three cycles were performed, initial discharge capacity was measured using PNE-0506 charge/discharge equipment (manufacturer: PNE SOLUTION Co., Ltd., 5 V, 6 A). Then, after each lithium secondary battery was charged to a state of charge (SOC) of 50%, initial resistance was calculated by a voltage drop obtained in a state in which each lithium secondary battery was subjected to a discharge pulse at 2.5 C for 10 seconds. The voltage drop was measured using PNE-0506 charge/discharge equipment (manufacturer: PNE SOLUTION Co., Ltd., 5 V, 6 A).

Subsequently, each lithium secondary battery was charged at 0.33 C rate to 4.20 V under a constant current-constant voltage (CC-CV) charging condition at 45° C., then subjected to 0.05 C current cut-off, and discharged at 0.33 C rate under a constant current condition to 2.5 V. The above charging and discharging were defined as one cycle, and 200 cycles of charging and discharging were performed at a high temperature (45° C.)

After 200 cycles, each lithium secondary battery was charged at 0.33 C rate under a constant current condition to 4.20 V, then subjected to 0.05 C current cut-off, and discharged at 0.33 C rate under a constant current condition to 2.5 V to measure discharge capacity after 200 cycles at 25° C. using PNE-0506 charge/discharge equipment (manufacturer: PNE SOLUTION Co., Ltd., 5 V, 6 A), this was substituted into the following [Equation 5] to measure a capacity retention, and the results thereof are presented in Table 6 below.

Also, direct current internal resistance (hereinafter, referred to as "DC-iR") was calculated by a voltage drop obtained in a state in which each lithium secondary battery was subjected to a discharge pulse at 2.5 C for 10 seconds at an SOC of 50%, this was substituted into the following [Equation 6] to calculate a resistance increase rate (%) after 200 cycles, and the results thereof are then presented in Table 6 below. The voltage drop was measured using PNE-0506 charge/discharge equipment (manufacturer: PNE SOLUTION Co., Ltd., 5 V, 6 A).

$$\text{Capacity retention (\%)} = \text{(discharge capacity after 200 cycles/initial discharge capacity)} \times 100 \quad \text{[Equation 5]}$$

$$\text{Resistance increase rate (\%)} = \{(\text{resistance after 200 cycles} - \text{initial resistance})/\text{initial resistance}\} \times 100 \quad \text{[Equation 6]}$$

TABLE 6

| | After 200 cycles at high temperature (45° C.) ||
| | Capacity retention (%) | Resistance increase rate (%) |
|---|---|---|
| Example 5 | 90.09 | 4.07 |
| Comparative Example 5 | 86.75 | 17.93 |

Referring to Table 6, with respect to the secondary battery of Example 5, since a stable film was formed on the surfaces of the positive electrode/negative electrode, it may be confirmed that capacity retention and resistance increase rate were significantly improved in comparison to those of Comparative Example 5 due to the suppression of additional electrolyte decomposition when long-term charge and discharge at high temperature were performed.

The invention claimed is:

1. A non-aqueous electrolyte solution for a lithium secondary battery, the non-aqueous electrolyte solution comprising:
   a lithium salt;
   an organic solvent;
   a compound represented by the following Formula 1a as a first additive; and
   lithium difluorophosphate as a second additive, wherein a weight ratio of the first additive to the second additive is in a range of 1:2 to 1:10

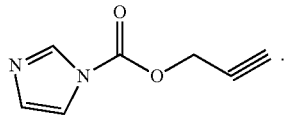

[Formula 1a]

2. The non-aqueous electrolyte solution for a lithium secondary battery of claim 1, wherein the first additive is included in an amount of 0.01 wt % to 5 wt % based on a total weight of the non-aqueous electrolyte solution.

3. The non-aqueous electrolyte solution for a lithium secondary battery of claim 2, wherein the first additive is included in an amount of 0.5 wt % to 3 wt % based on the total weight of the non-aqueous electrolyte solution.

4. The non-aqueous electrolyte solution for a lithium secondary battery of claim 1, wherein the weight ratio of the first additive to the second additive is in a range of 1:2 to 1:5.

5. The non-aqueous electrolyte solution for a lithium secondary battery of claim 1, further comprising at least one third additive of a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, or a lithium salt-based compound.

6. The non-aqueous electrolyte solution for a lithium secondary battery of claim 5, wherein the third additive is present in an amount of 0.01 wt % to 10 wt % based on a total weight of the non-aqueous electrolyte solution.

7. A lithium secondary battery, comprising:

a positive electrode;

a negative electrode;

a separator; and the non-aqueous electrolyte solution of claim 1.

* * * * *